(12) United States Patent
Roh et al.

(10) Patent No.: US 11,571,266 B1
(45) Date of Patent: Feb. 7, 2023

(54) ROBOTIC SURGICAL SYSTEM FOR INSERTION OF SURGICAL IMPLANTS

(71) Applicant: IX Innovation LLC, Seattle, WA (US)

(72) Inventors: Jeffrey Roh, Seattle, WA (US); Justin Esterberg, Mercer Island, WA (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/547,678

(22) Filed: Dec. 10, 2021

(51) Int. Cl.
*A61B 34/32* (2016.01)
*A61B 34/10* (2016.01)

(52) U.S. Cl.
CPC ............ *A61B 34/32* (2016.02); *A61B 34/10* (2016.02); *A61B 2034/105* (2016.02); *A61B 2034/107* (2016.02)

(58) Field of Classification Search
CPC ......... A61B 34/32; A61B 34/35; A61B 34/37; A61B 34/10; A61B 2034/101; A61B 2034/102; A61B 2034/104; A61B 2034/105; A61B 2034/107; A61B 2034/108; A61B 2034/20

USPC ............................................................ 606/1
See application file for complete search history.

(56) References Cited

U.S. PATENT DOCUMENTS

| 11,112,770 B2* | 9/2021 | Roh ................... G16H 50/50 |
| 11,166,764 B2* | 11/2021 | Roh ................... A61B 34/20 |
| 11,304,760 B1* | 4/2022 | Roh ................... A61B 90/98 |
| 11,389,248 B1* | 7/2022 | Roh ................... A61B 34/30 |
| 2015/0088293 A1* | 3/2015 | Metzger ............. A61F 2/5046 700/98 |
| 2017/0312031 A1* | 11/2017 | Amanatullah ........ A61B 34/10 |
| 2019/0029757 A1* | 1/2019 | Roh ................... A61B 34/10 |
| 2020/0030034 A1* | 1/2020 | Kontaxis .............. A61F 2/3094 |
| 2022/0241021 A1* | 8/2022 | Spaelter .............. A61B 90/37 |

* cited by examiner

*Primary Examiner* — Ahmed M Farah
(74) *Attorney, Agent, or Firm* — Perkins Coie LLP

(57) ABSTRACT

Methods, apparatuses, and systems for robotic insertion of a screw, a rod, or another component of a surgical implant into a patient are disclosed. Clinical data from previous surgical procedures or information received from a supervising surgeon can be leveraged to minimize the risk of harm to the patient and improve outcomes. The methods disclosed thus provide more precise placement of implanted surgical components and implants.

20 Claims, 9 Drawing Sheets

| Action ID | Action | Implant ID | Patient ID | Age | Gender | Screw Depth (in.) | Rotational Speed (RPM) | Axial Force (PSI) |
|---|---|---|---|---|---|---|---|---|
| INS-SCRW-0321 | Insert Screw | SF-00345 | 32163 | 35 | Male | 1.5 | 15 | 4 |
| INS-SCRW-0845 | Insert Screw | SF-02345 | 35468 | 64 | Male | 2 | 18 | 4 |
| INS-SCRW-1654 | Insert Screw | SF-10345 | 13254 | 54 | Female | 1.5 | 13 | 6 |
| INS-SCRW-1356 | Insert Screw | SF-02348 | 23546 | 47 | Female | 1 | 5 | 3 |
| INS-SCRW-0645 | Insert Screw | SF-00034 | 34658 | 25 | Male | 1.5 | 9 | 5 |
| INS-SCRW-0816 | Insert Screw | SF-00215 | 20314 | 38 | Male | 2 | 12 | 4 |

ROBOTIC SURGICAL SYSTEM FOR INSERTION OF SURGICAL IMPLANTS

TECHNICAL FIELD

The present disclosure is generally related to automated and robotic surgical procedures and specifically to systems and methods for robotic insertion of surgical implants.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure as well as technical surgical errors during the operation. For example, adverse events can occur due to (i) breakdown in communication within and among the surgical team, care providers, patients, and their families; (ii) delay in diagnosis or failure to diagnose; and (iii) delay in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

DETAILED DESCRIPTION

Figure 1:
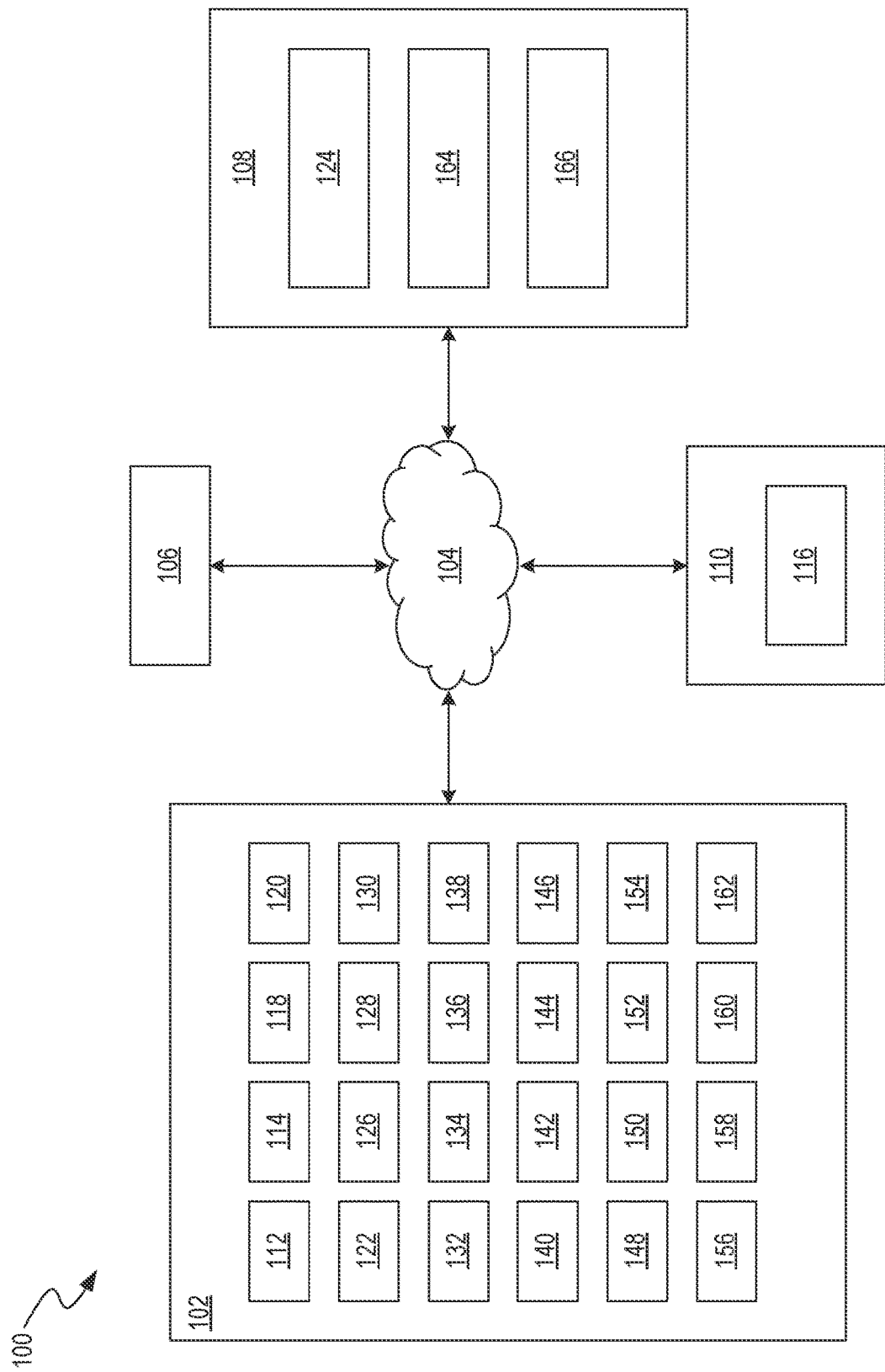
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples.

These and other aspects, features, and implementations can be expressed as methods, apparatus, systems, components, program products, means or steps for performing a function, and in other ways.

These and other aspects, features, and implementations will become apparent from the following descriptions, including the claims.

A surgical implant refers to a medical device manufactured to replace a missing biological structure, support a damaged biological structure, or enhance an existing biological structure. Traditional surgical tools are primarily assistive devices to help surgeons by compensating for tremors, increasing the precision of movement, and providing access to the patient in a less invasive manner which would otherwise not be possible. However, traditional surgical tools are typically unable to perform critical surgical actions, instead relying on a surgeon to take the most significant actions. For example, when inserting a screw into a bone, a surgeon relies on human clinical judgement to determine whether the screw has been implanted completely or they are receiving an unacceptable amount of resistance where continuing may risk harming the patient. Traditional methods therefore result in a wide range of variability among surgeons.

Moreover, surgeons require a significant amount of training in addition to experience before becoming proficient, and often require a similar level of dedication for each type of procedure they master. As such, generalized surgeons are rare and some procedures only have a small handful of people worldwide capable of performing them due to the rarity of some procedures.

The embodiments disclosed herein describe methods, apparatuses, and systems for robotic insertion of surgical implants. In some embodiments, by one or more imaging devices of a surgical system image a patient's body for inserting a surgical implant in the patient's body. The surgical implant includes at least one surgical implant component. One or more processors of the surgical system generate a virtual model of the patient's body. The virtual model represents at least an implantation site for the surgical implant. The one or more processors generate an implantation plan based on the virtual model. The implantation plan includes insertion parameters for controlling a surgical robot of the surgical system. The one or more processors modify the insertion parameters based on a comparison of the insertion parameters to stored insertion parameters retrieved from a surgical procedure database using a regression model. The surgical robot inserts the at least one surgical implant component in the patient's body in accordance with the insertion parameters.

The advantages and benefits of the methods, systems, and apparatus disclosed herein include compatibility with best practice guidelines for performing surgery in an operating room, e.g., from regulatory bodies and professional standards organizations such as the Association for Surgical Technologists. The robotic surgical system disclosed can use multiple transducers and other measurement instrumentation to monitor the insertion of a screw with a higher degree of precision that is beyond the capabilities of a surgeon. Further, the robotic surgical system disclosed is not overwhelmed by receiving multiple measurement readings whereas a surgeon having to monitor multiple readings, such as axial force, tool speed, etc., while inserting a screw is likely to be overwhelmed or distracted. The robotic surgical system disclosed can automates steps of surgical procedures to compensate for a lack of a surgeon's experience with a specific procedure and make surgery more accessible. Moreover, the automated methods for inserting surgical implant components in a patient facilitate more precise placement of implant hardware while reducing opportunities for human error. The disclosed automation methods can serve as a prerequisite for achieving remote surgery capabilities where a surgeon may not be present in an operating room with a patient. Further benefits include improved control of insertion parameters such as preventing too much force from being used that can cause complications during an insertion procedure.

The robotic surgery technologies disclosed further offer valuable enhancements to medical or surgical processes through improved precision, stability, and dexterity. The disclosed methods relieve medical personnel from routine tasks and make medical procedures safer and less costly for patients. The embodiments disclosed enable performing more accurate surgery in more minute locations on or within the human body. The embodiments also and address the use of dangerous substances. The adoption of robotic systems, according to the embodiments disclosed herein, provides several additional benefits, including efficiency and speed improvements, lower costs, and higher accuracy. The equipment tracking system integrated into the disclosed embodiments offers flexibility and other advantages, such as requiring no line-of-sight, reading multiple radio frequency identification (RFID) objects at once, and scanning at a distance. The advantages offered by the surgical tower according to the embodiments disclosed herein are smaller incisions, less pain, lower risk of infection, shorter hospital stays, quicker recovery time, less scarring, and reduced blood loss. The advantages of the convolutional neural network (CNN) used for machine learning (ML) in the disclosed embodiments include the obviation of feature extraction and the use of shared weight in convolutional layers, which means that the same filter (weights bank) is used for each node in the layer; this both reduces memory footprint and improves performance.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or outpatient surgery center.

In some embodiments, the system 100 includes one or more medical or surgical patient monitors 112. The monitors 112 can include a vital signs monitor (a medical diagnostic instrument), which can be a portable, battery powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiologic parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end tidal CO2 monitor or capnography monitor used for measurement of the level of carbon dioxide that is released at the end of an exhaled breath (referred to as end tidal carbon dioxide, ETCO2). An end tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end tidal CO2 monitor can be configured as side stream (diverting) or mainstream (non-diverting). A diverting end tidal CO2 monitor transports a portion of a patient's respired gases from the sampling site to the end tidal CO2 monitor while a non-diverting end tidal CO2 monitor does not transport gas away. Also, measurement by the end tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in artery, used in the operating room 102) for measurement. The non-invasive method (referred to as a sphygmomanometer) works by measurement of force exerted against arterial walls during ventricular systole (i.e., systolic blood pressure occurs when the heart beats and pushes blood through the arteries) and ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate, which is the rate at which breathing occurs, and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can bring a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia where the heart rate becomes faster and bradycardia where the heart rate becomes slower), coronary heart disease, heart attacks, or cardiomyopathy. The instrument used for measurement of the electrocardiogram is called an electrocardiograph which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which help in guiding the surgeon during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP), the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG), the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation, and does not perform external stimulation. Spontaneous EMG is recorded by the insertion of a needle electrode. Triggered EMG refers to the recording of myoelectric signals during stimulation of a target site such as pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end-effectors, cameras mounted to the ceiling or other surface above the surgical theater, or cameras mounted on a tripod or other independent mounting device. In some embodiments, the cameras are body worn by a surgeon or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by performing a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. The doctor moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgeon makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals over long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors comprise a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles which allow the surgeon to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engages with one another. When a telescope is used to operate on the abdomen, the procedure is called laparoscopy. The surgical tower 128 typically includes access to a variety of surgical tools, such as, for example, electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles) which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument can 130 consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools and minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool—tissue interaction forces. During MIS, the field of view and workspace of surgical tools are compromised due to the indirect access to the anatomy and lack of surgeon's hand-eye coordination. The sensors 134 provide a tactile sensation to the surgeon by providing information of shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used can be brain/spinal cord anomalies, tumors in the body, breast cancer screening, joint injuries, uterine/pelvic pain detection, or heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI can more widely suit for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"— of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer which produces sound waves and sends them into the body. The sound waves that are reflected are converted into electrical signals which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for the fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgeons in the placement of specialized surgical instruments and implants. The patient images are taken to guide the physician before or during the medical procedure. The stereotactic navigation system 138 includes a camera having infrared sensors to determine the location of the tip of the probe being used in the surgical procedure. This information is sent in real-time so that the surgeons have a clear image of the precise location where they are working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a postoperative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table which is designed for use in spinal surgeries and can be used in a variety of spinal procedures in supine, prone, or lateral positions in a safe manner. Two peculiar features of the Jackson table 144 are no central table support and an ability to rotate the table through 180 degrees. The Jackson table 144 is supported at both ends which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets which cover the patient. The blanket can be designed to use pressure points on the patient's body to prevent heat from reaching areas at risk for pressure sores or burns. The blanket can also include drain holes where fluid passes through the surface of the blanket to linen underneath which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors which can contribute to poor quality in the environment of the operating room 102 are temperature, ventilation, and humidity, and those conditions can lead to profound effects on the health and work productivity of people in the operating room 102. As an example: surgeons prefer a cool, dry climate since they work in bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter. High-Efficiency Particulate Air filter (HEPA filter) protects from infection and contamination by a filter which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system which controls the muscles). A major percentage of orthopedic tools are made of plastic. The orthopedic tools can be divided into the following specialties: hand and wrist, foot and ankle, shoulder and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can comprise a physical drill, power cord, electronically motorized bone drill, or rotating bone shearing incision work unit.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be of type absorbable (the stitches automatically break down harmlessly in the body over time without intervention) and non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as sensor/transducer, signal conditioner, display, data storage unit, etc. In some embodiments, the medical equipment includes a sensor to receive a signal from a measurand/patient; a transducer for converting one form of energy to electrical energy; a signal conditioner such as an amplifier, filter, etc., to convert the output from the transducer into an electrical value; a display to provide a visual representation of the measured parameter or quantity; and a storage system to store data which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allows it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc.

The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. CPAP instrument can comprise a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment 102. The consumables 158 can include gloves, gowns, masks, syringes, needles, sutures, staples, tubing, catheters, or adhesives for wound dressing, in addition to other surgical tools needed by doctors and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries are performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR are a digital version of patients' paper charts. The EHR database 106 can contain more information than a traditional patient chart, including, but not limited to, a patients' medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

Figure 2:
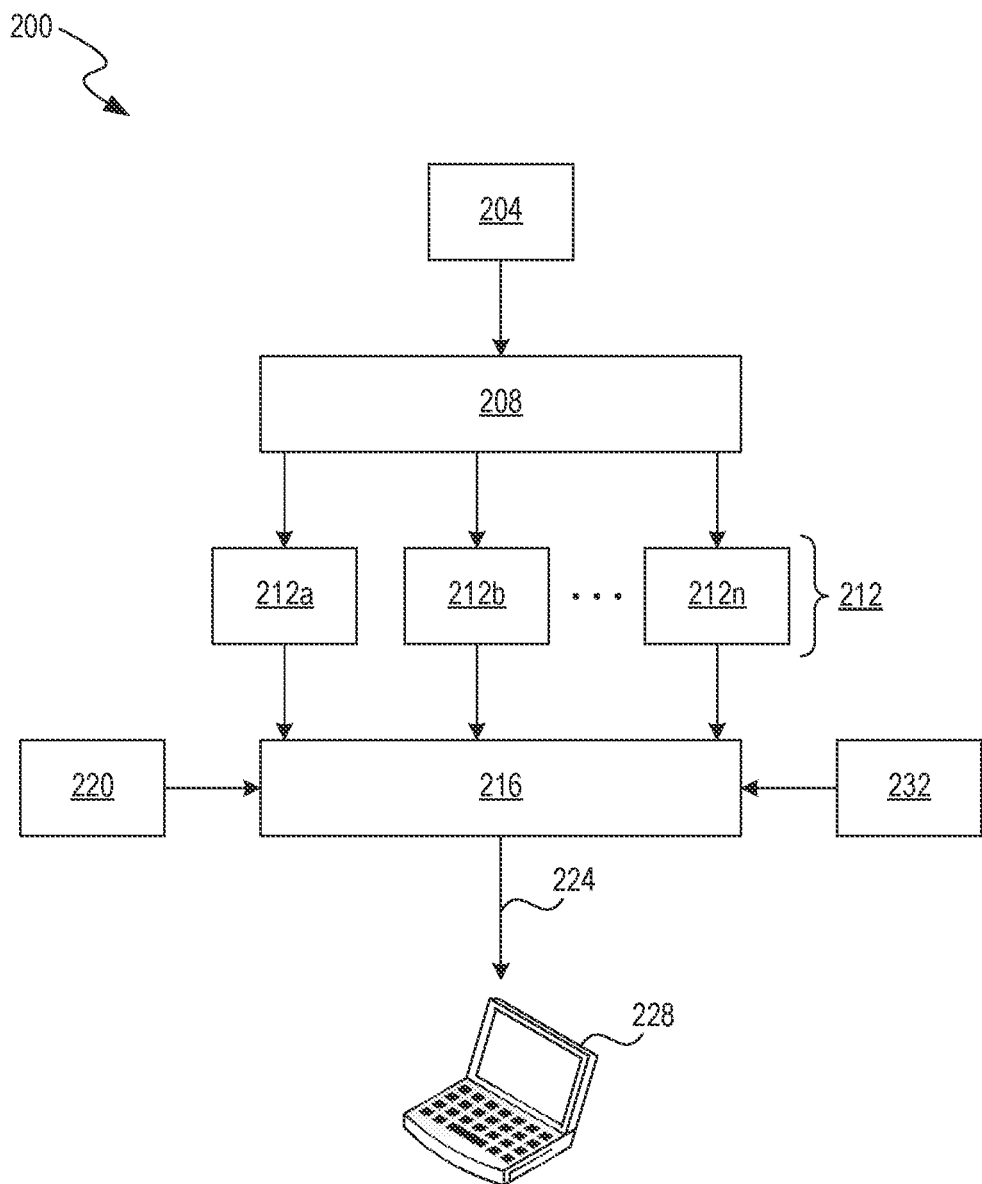
FIG. 2 is a block diagram illustrating an example machine learning (ML) system, in accordance with one or more embodiments.

FIG. 2 is a block diagram illustrating an example machine learning (ML) system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . , 212n. The feature extraction module 208 reduces the redundancy in the input data 204, e.g., repetitive data values, to transform the input data 204 into the reduced set of features 212, e.g., features 212a, 212b, . . . , 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place.

Figure 3:
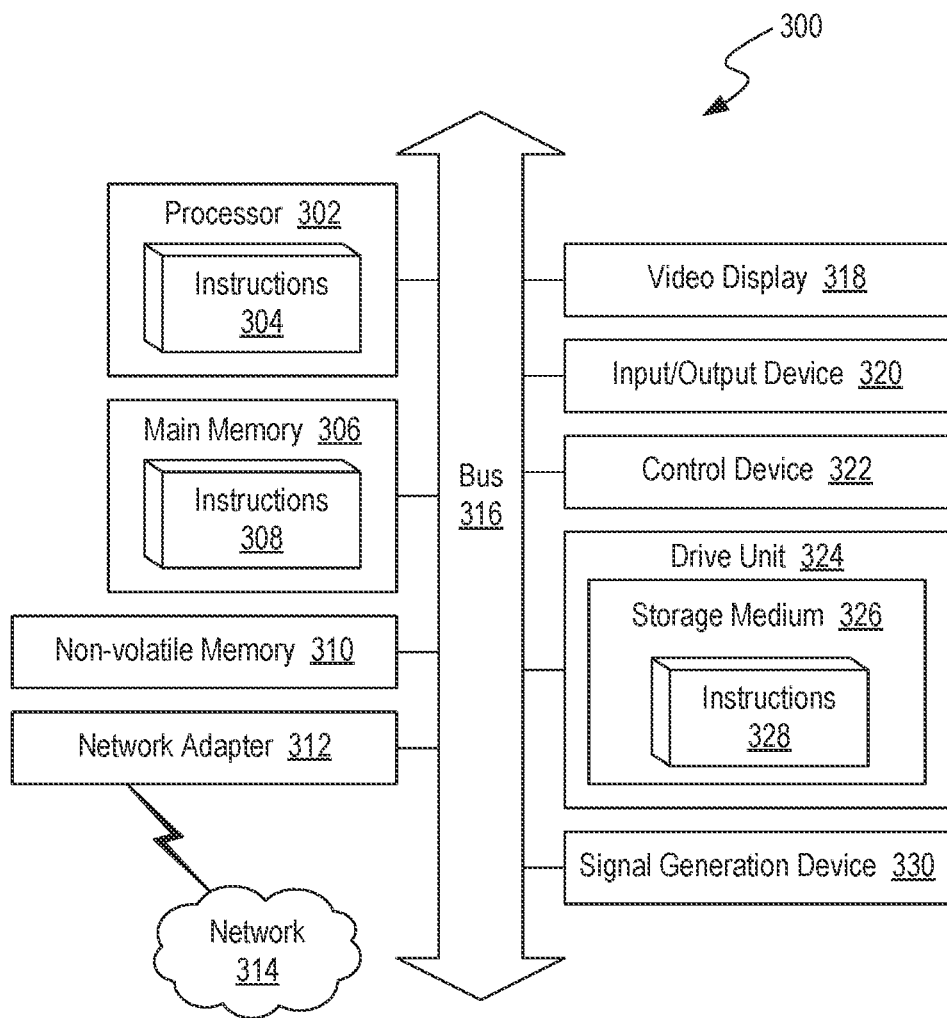
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multi-layer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
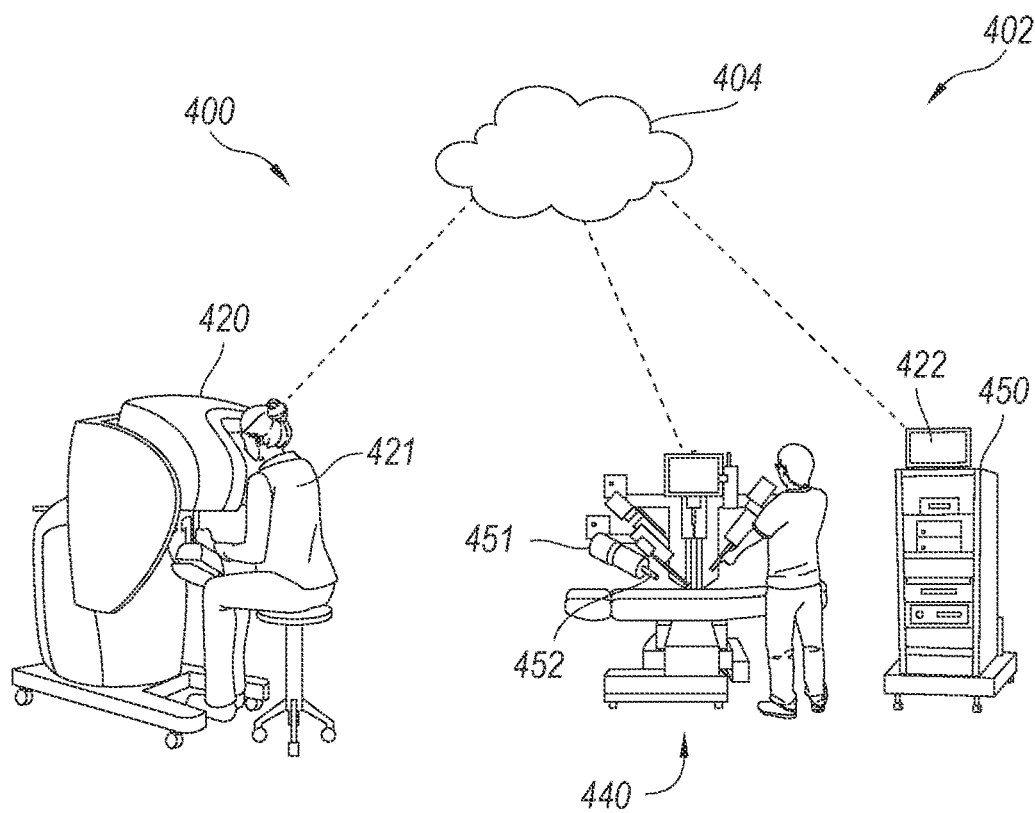
FIG. 4A is a block diagram illustrating an example robotic surgical system, in accordance with one or more embodiments.

FIG. 4A is a block diagram illustrating an example robotic surgical system 400, in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1).

The robotic surgical system 400 includes a user device or console 420 ("console 420"), a surgical robot 440, and a computer or data system 450. The console 420 can be operated by a surgeon and can communicate with components in an operating room 402, remote devices/servers, a network 404, or databases (e.g., database 106 of FIG. 1) via the network 404. The robotic surgical system 400 can include surgical control software and can include a guidance system (e.g., ML guidance system, AI guidance system, etc.), surgical planning software, event detection software, surgical tool software, etc. or other features disclosed herein to perform surgical step(s) or procedures or implement steps of processes discussed herein.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to medical images, video, etc. For surgical applications, the images could include, but are not limited to, real-time optical images, real-time ultrasound, real-time OCT images and/or other modalities, or could include preoperative images, such as MRI, CT, PET, etc. The various imaging modalities can be selectable, programmed, superimposed and/or can include other information superimposed in graphical and/or numerical or symbolic form.

The robotic surgical system 400 can include multiple consoles 420 to allow multiple users to simultaneously or sequentially perform portions of a surgical procedure. The number and configuration of consoles 420 can be selected based on the surgical procedure to be performed, number and configurations of surgical robots, surgical team capabilities, or the like.

Figure 4B:
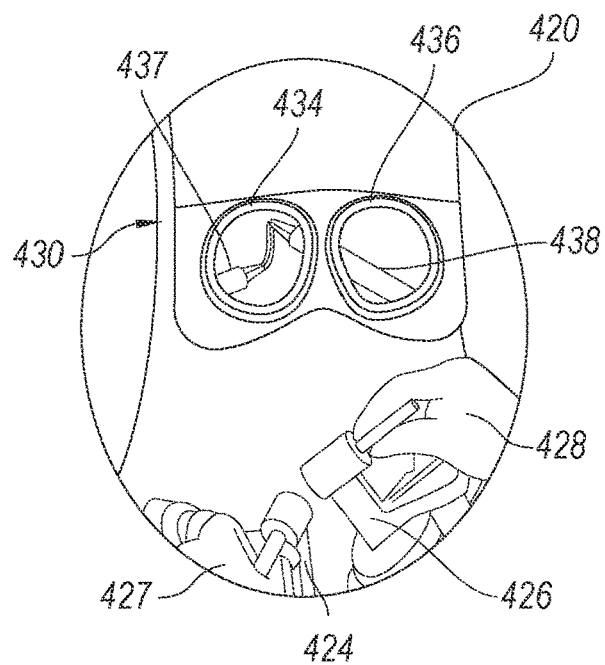
FIG. 4B illustrates an example console of the robotic surgical system of FIG. 4A, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452.

In an autonomous mode, the surgical robot 440 can autonomously perform steps under the control of the data system 450. The robotic surgical system 400 can be pre-programmed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include physician input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring.

In some embodiments, the robotic surgical system 400 can determine whether a detected event is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like.

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre- or post-operative virtual simulations, simulations using models, etc.) can be generated and collected.

The surgical robot 440 can include robotic arms 451 (one identified) with integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein.

The robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or minimally invasive surgery. One example of a surgical system and surgical robots which can incorporate methods and technology is the DAVINCI™ system available from Intuitive Surgical, Inc.™ of Mountain View, Calif. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modified, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operative or intraoperatively.

Embodiments can provide a means for mapping the surgical path for neurosurgery procedures that minimize damage through artificial intelligence mapping. The software for artificial intelligence is trained to track the least destructive pathway. The physician can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and posttreatment mapping can be compared by the surgeon and/or ML/AI system. The comparison can be used to determine next steps in a procedure and/or further train the ML/AI system.

Figure 5:
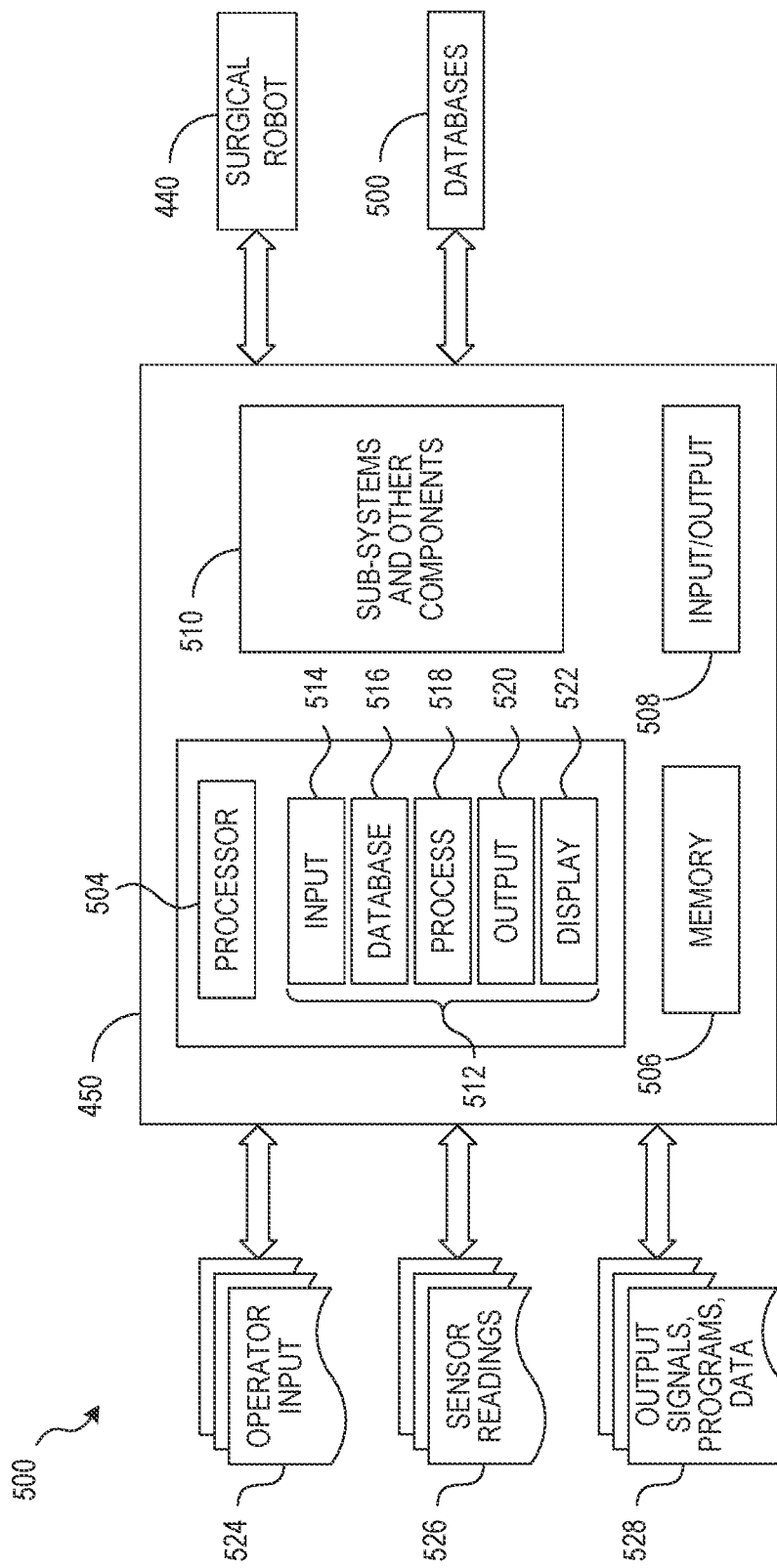
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices, and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field programmable gate array, or secure application-specific integrated circuit. The memory 506 can store instructions for causing the surgical robot 440 to perform acts disclosed herein.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. For example, if an applicator moves an undesirable amount during a treatment session, the input/output device 508 can alert the subject and/or operator via an audible alarm. The input/ output device 508 can be a touch screen that functions as both an input device and an output device.

The data system 450 can output instructions to command the surgical robot 440 and communicate with one or more databases 2600. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between surgical equipment within the surgical room.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

Figures 6, 7:
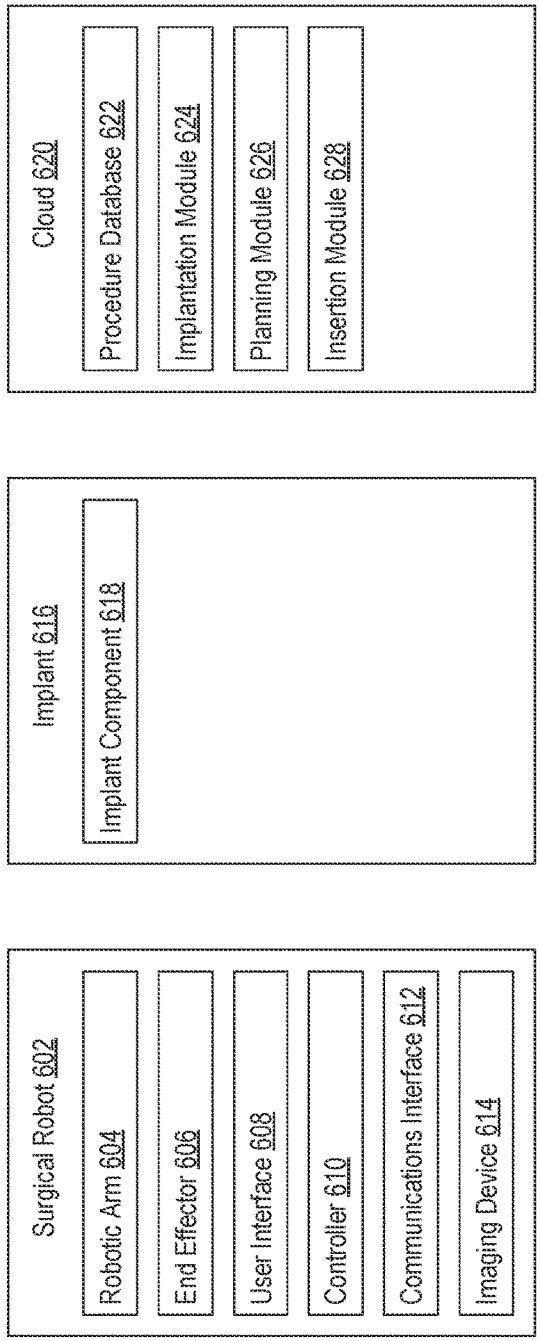
FIG. 6 is a block diagram illustrating an example robotic surgical system for insertion of surgical implants, in accordance with one or more embodiments.
FIG. 7 is a table illustrating an example surgical procedure database, in accordance with one or more embodiments.

FIG. 6 is a block diagram illustrating an example robotic surgical system for insertion of surgical implants, in accordance with one or more embodiments. The insertion of surgical implants or surgical implant components is sometimes referred to as "implantation." The system includes a surgical robot 602, databases and modules that can be implemented in the cloud 620, and one or more implants 616. The surgical robot 602 is the same as or similar to the surgical robot 440 illustrated and described in more detail with reference to FIG. 4A. The system is implemented using the components of the example computer system 300 illustrated and described in more detail with reference to FIG. 3. Likewise, embodiments of the system can include different and/or additional components or can be connected in different ways.

The surgical robot 602 is a robotic system designed to assist a surgeon in performing a surgical operation or procedure on a patient. The surgical robot 602 includes at least one controller 610 and at least one robotic arm 604 having an end effector 606 or at least one imaging device 614. The surgical robot 602 can further include a user interface 608 for accepting control inputs from a user, such as a surgeon or other medical professional, and a communications interface 612 for transmitting and receiving data to and from a cloud 620 for the purpose of training an artificial intelligence (AI) or machine learning (ML) model operating within the surgical robot 602 or receiving remote commands from a remote user or an AI existing external to the surgical robot 602. The robotic arm 604 is a mechanically actuated arm or lever having at least two degrees of freedom. The robotic arm 604 includes at least one end effector 606 or at least one imaging device 614, and can include both an end effector 606 and at least one imaging device 614. The robotic arm 604 can change the end effector 606 to facilitate multiple functions and operation of a variety of surgical tools 154. The surgical tools 154 are illustrated and described in more detail with reference to FIG. 1.

The robotic arm 604 can be manually controlled or operated in an autonomous or semi-autonomous mode. The surgical robot 602 can have one robotic arm 604 or multiple robotic arms 604, each of which can be operated independently by one or more users or autonomous systems or a combination of users and autonomous systems. The end effector 606 is the end of the robotic arm 604 that is conducting work. The end effector 606 is typically a tool or device for interacting with a physical object and may be a surgical tool 154 intended for acting upon or within a patient's body or can be a gripping device for securing a separate surgical tool 154 to the robotic arm 604. The end effector 606 can be permanently affixed to the end of the robotic arm 604 or can be detachable, allowing for a system of interchangeable end effectors 606, which are alternatively selected and swapped by a single robotic arm 604 or multiple robotic arms 604.

The user interface 608 is a means of interacting with the surgical robot 602 and can include any of a keyboard, computer mouse, trackball, joystick, wireless or wired gamepad, sliders, scroll wheels, touch screen or microphone for receiving voice commands. The user interface 608 can additionally include other methods of interaction of a user with the surgical robot 602. The user interface 608 can accept direct inputs, such as from a joystick controlling the movement of the robotic arm 604 or indirect inputs such as commands entered on a keyboard or touch screen such as adjusting the sensitivity of a joystick control or the speed of a robotic arm 604's movement in response to a joystick.

The controller 610 is a computing device including a processor for completing computations and a memory component for storing data for use in computations. The memory can store data temporarily such as for intermediate values used by the controller 610 to complete complex computations or may additionally comprise persistent storage for longer term storage of information. The controller 610 is in communication with the communications interface 612 and can further control the at least one robotic arm 604 and end effector 606 of the surgical robot 602. The communications interface 612 allows the surgical robot 602 to communicate with external devices and can include a wireless antenna and transceiver or a port for receiving a cable to facilitate a wired connection. Examples of a wired connection include ethernet, universal serial bus (USB) or a proprietary connection. A wireless communications interface may include any of Wi-Fi, Bluetooth, near field communications (NFC) or a cellular communications interface such as 3G, 4G, LTE, or 5G. The communications interface 612 can connect a user interface to the surgical robot 602 or facilitate access to a local network or the cloud network to access a remote server and/or database.

In some embodiments, at least one imaging device 614 of the surgical system of FIG. 6 image at least a portion of a patient's body for inserting the surgical implant 616 in the patient's body. The surgical implant includes at least one surgical implant component 618. The imaging device 614 is any device capable of detecting sound or electromagnetic waves and assembling a visual representation of the detected waves. The at least one imaging device 614 can collect waves from any part of the electromagnetic spectrum or sounds at any range of frequencies, often as a matrix of independently acquired measurements which each represent a pixel of a two or three-dimensional image. These measurements can be taken simultaneously or in series via a scanning process or a combination of methods. Some pixels of an image produced by the imaging device 614 can be interpolated from direct measurements representing adjacent pixels in order to increase the resolution of a generated image. The imaging devices 614 can include, or receive or generate imaging data from multiple devices. The multiple devices can include, for example, cameras attached to the robotic arm 604, cameras mounted to the ceiling or other above the surgical theater, cameras mounted on a tripod or other independent mounting device, cameras that are bodily worn by the surgeon or other surgical staff, cameras that are incorporated into a wearable device, such as an augmented reality device (e.g., Google Glass™), cameras that are integrated to an endoscopic, microscopic, laparoscopic, or any camera or other imaging device (e.g., an ultrasound) that is present in the surgical theater. The imaging device 614 can execute an algorithm or software module capable of extracting qualitative or quantitative data from medical images. The algorithm or software module can be, for example, a deep learning algorithm that has been trained on a data set of medical images (see FIG. 2).

The one or more surgical implants 616 (sometimes referred to as implants) are therapeutic prosthetic devices intended to reinforce or restore functionality to a part of a body that has been impacted by an injury, typically traumatic, or a degenerative disease which can result in the loss or destruction of a part of the body. The surgical implants 616 can be rigid, such as when reinforcing bone structures, or can be flexible, such as when replacing or supplementing soft tissues. Similarly, a surgical implant 616 can be static and unmoving, or can include articulating joints or other moveable elements. A surgical implant 616 can include any of a range of materials, each of which can have different properties, such as being rigid or flexible. Multiple materials can be utilized in different surgical implant components 618 (sometimes referred to as implant components) or at a location where surgical implant components 618 meet to perform different functions creating more complex surgical implants. The surgical implant 616 can be a single piece or include multiple surgical implant components 618. Surgical implants including multiple surgical implant components 618 can alternatively be referred to as assemblies. The surgical implants 616 are typically customized to fit a patient and the specific application the surgical implant 616 is intended for.

In some embodiments, the surgical implant 616 includes biological donor tissues or biosynthetic tissues, such as can be used in operations such as organ transplant, skin graft, or other tissue implantation or replacement. In other embodiments, the surgical implant 616 includes any of multiple implantable medical devices, for example, cardiac pacemakers, electric neurological stimulation devices such as vagus nerve stimulators or deep brain stimulators, blood glucose monitors, insulin pumps, etc. The one or more surgical implant components 618 are each single manufacturable components of the surgical implant 616. The surgical implant components 618 include subassemblies, such as hinges, balls, and sockets to create joints or simple components such as screws, rods, plates, and other components which may be included in a surgical implant 616. The surgical implant components 618 can be customized when manufactured, or alternatively, before or during insertion.

The cloud 620 is a distributed network of computers including servers and databases. The cloud 620 can be a private cloud, where access is restricted by isolating the network such as preventing external access, or by using encryption to limit access to only authorized users. Alternatively, the cloud 620 can be a public cloud where access is widely available via the internet. A public cloud may not be secured or may include limited security features. The surgical procedure database 622 stores data from previous implant insertion procedures. The data can describe patient data, the previously implanted implants and implant components, previous patient outcomes, surgical tool path and implant insertion parameters. In some embodiments, one or more processors of the surgical system of FIG. 6 generate a virtual model of a portion of the patient's body based on the imaging. In other embodiments, the processors of the surgical system generate the virtual model based on other images, such as X-ray, fluoroscopy, MRI, ultrasound, endoscopy, elastography, tactile imaging, thermography, medical photography, or nuclear medicine images, e.g., PET (see FIG. 1).

The virtual model represents at least an implantation site for the surgical implant 616. The path for the surgical tools 154 or the surgical implant 616 refers to the allocation of a schedule to individual surgical tools 154 or the surgical implant 616 over a given set of locations in a virtual model of a portion of the patient's body or across the patient's body. The path for the surgical tools 154 or the surgical implant 616 is sometimes referred to as a pathing. The surgical procedure database 622 is populated by the implantation module 624, a user device operated by a medical professional, or additional data sources such as surgeons, physicians, nurses, and surveys of patients to assess their individual patient outcomes. The surgical procedure database 622 can be located in the cloud 620, a local server, or on a discrete device.

The implantation module 624 installs the surgical implant 616 in or on the patient's body. In some embodiments, one or more processors of the surgical system of FIG. 6 generate an implantation plan based on the virtual model. The implantation plan includes insertion parameters for controlling the surgical robot 602. The implantation module 624 receives the implantation plan from the planning module 626, and alternatively, prompts the insertion module 628 to complete the automated insertion of the implant components 618 or other automated action, prompts a surgeon to manually perform a surgical action, or prompts a user device operated by a medical professional. The implantation plan is the same as or similar to the surgical plan illustrated and described in more detail with reference to FIG. 4B. The implantation plan is sometimes referred to as a surgical implant implantation plan, an implant plan, or a surgical implant plan. The steps included in the implantation plan are performed until none remain and the insertion procedure is complete. The planning module 626 generates the implantation plan.

The patient is imaged using the at least one imaging device 614, and a virtual model of a portion of the patient's body. The virtual model can include the entirety of the patient's body, or alternatively, only a part of the patient's body. The implant components 618 are placed within the virtual model and tool path is generated. Additionally, insertion parameters are generated that can be used by the insertion module 628 to control the path of a surgical tool 154 or implant 616, the speed at which the surgical tool 154 moves, the orientation of an implant component 618, or the axial forces to be applied. The insertion parameters can be discrete values or ranges of acceptable values. The insertion module s28 controls the automated insertion of an implant component 618 into the patient's body when prompted by the implantation module 624. The insertion module 628 uses data from the surgical procedure database 622 to optimize the insertion parameters originally defined in the planning module 626. Alternatively, the insertion parameters can be generated during other steps, such as imaging, placement design, path design, or implant insertion. In some embodiments, the imaging device 614 comprises a real time imaging device used in surgery, such as an endoscope or other surgical imaging device. In such an embodiment, the real time imaging data from imaging device 614 can be used to update the virtual model of the at least a portion of the patient's body. The updated model can be used to adjust the location of implant components 618, the path of the surgical tool 154 or implant 616, the speed at which the surgical tool 154 moves, the orientation of an implant component 618, or the axial forces to be applied.

In embodiments, one or more processors of the surgical system of FIG. 6 generate a path for a surgical tool 154 of the surgical system of FIG. 6 in the virtual model of a portion of the patient's body to virtually insert the surgical implant 616 at the implantation site of the virtual model. The one or more processors can perform a virtual robotic surgical procedure for the surgical robot 602 according to the implantation plan to virtually insert the at least one surgical implant component 618 at the implantation site using the path for the surgical tool 154. The virtual robotic surgical procedure for the surgical robot 602 is performed using simulation and computer-aided design. For example, the virtual robotic surgical procedure is performed using the one or more processors to aid in the creation, modification, analysis, or optimization of the surgical implant 616, and to create a database for manufacturing. Further, the virtual robotic surgical procedure can use either vector-based graphics to depict the surgical implant 616, or can also produce raster graphics showing the overall appearance and path of the surgical implant 616 in the virtual robotic surgical procedure. Moreover, the output of the virtual robotic surgical procedure can convey information, such as processes, dimensions, and tolerances, according to application-specific conventions. The virtual robotic surgical procedure can be used to design curves and figures in two-dimensional (2D) space or curves, surfaces, and solids in three-dimensional (3D) space, and to rotate and move a virtual model of the surgical implant 628 for viewing.

Simulations for the virtual robotic surgical procedure can be performed using virtual models that can include two or three-dimensional models to evaluate, for example, one or more steps of a surgical procedure (or entire procedure), predicted events, outcomes, etc. The simulations can be used to identify and assess access paths, stresses, strains, deformation characteristics (e.g., load deformation characteristics, load distributions, etc.), fracture characteristics (e.g., fracture toughness), fatigue life, etc. The virtual model can include a model of the patient's anatomy, implant(s), end effectors, instruments, access tools, or the like. The one or more processors can generate a three-dimensional mesh to analyze models. Machine learning techniques to create an optimized mesh based on a dataset of anatomical features and implants or other devices. The three-dimensional models, surfaces, and virtual representations can be generated by computer-aided design (CAD) software, finite element analysis (FEA) software, and robotic control software/programs based on patient data (e.g., images, scans, etc.), implant design data, or the like. A user can view, manipulate (e.g., rotate, move, etc.), modify, set parameters (e.g., boundary conditions, properties, etc.) and interact with the models. The control parameters, robotic kinematics, and functionality can be used to generate the simulations. In some embodiments, models of end effectors of a robotic system and generated to perform virtual procedures on virtual anatomical models.

In embodiments, the surgical robot 602 inserts the at least one surgical implant component 618 in the patient's body in accordance with the insertion parameters. Inserting the at least one surgical implant component 618 can include controlling, by the surgical robot 602, a path of the at least one surgical implant component 618 in the patient's body based on the insertion parameters. Inserting the at least one surgical implant component 618 can include controlling, by the surgical robot 602, an orientation of the at least one surgical implant component 618 in the patient's body based on the insertion parameters. Inserting the at least one surgical implant component 618 can include controlling, by the surgical robot 602, an axial force applied to the at least one surgical implant component 618 in the patient's body based on the insertion parameters. In other embodiments, inserting the surgical implant 616 includes controlling, by the surgical robot 602, at least one of a path or a speed of a surgical tool 154 in the patient's body based on the insertion parameters.

A surgeon or a user device operated by a medical professional can monitor and the insertion parameters and can intervene if necessary. In embodiments, the insertion module 628 enables insertion of the implant component 618 into the patient's body while determining that the current insertion parameters measured in real-time are within the range of acceptable insertion parameters approved of by the surgeon or a user device operated by a medical professional. The insertion of an implant component 618 can additionally refer to any other step in the surgical procedure, including making incisions, responding to bleeding, or simply controlling the movement of a surgical tool 154 or imaging device 614, and does not require an implant component 618 to be involved.

FIG. 7 is a table illustrating an example surgical procedure database 622, in accordance with one or more embodiments. The surgical procedure database 622 is illustrated and described in more detail with reference to FIG. 6. The surgical procedure database 622 stores data from previous surgical implant insertion procedures. The surgical procedure database 622 stores data describing previously implanted implants and implant components, the previous tool path used during insertion procedures, previous insertion parameters, and previous patient information including gender, age, height, weight, medical conditions, patient medical history, patient family medical history, allergies, and vital information such as baseline measurements of heart rate, blood pressure, blood oxygen saturation and respiration rate. Likewise, embodiments of the surgical procedure database 622 can include different and/or additional rows, columns, and fields or can be addressed and linked in different ways.

The surgical procedure database 622 is populated with data from the implantation module 624, a user device operated by a medical professional, or medical professionals such as surgeons, physicians, nurses, and physical therapists, and from surveys of patient outcomes that evaluate the success of previous implant insertion procedures. The surgical procedure database 622 is used by the insertion module 628 to determine optimal implant parameters for inserting an implant component 618 or, alternatively, providing other automated actions, such as maneuvering a surgical tool 154.

Figure 8:
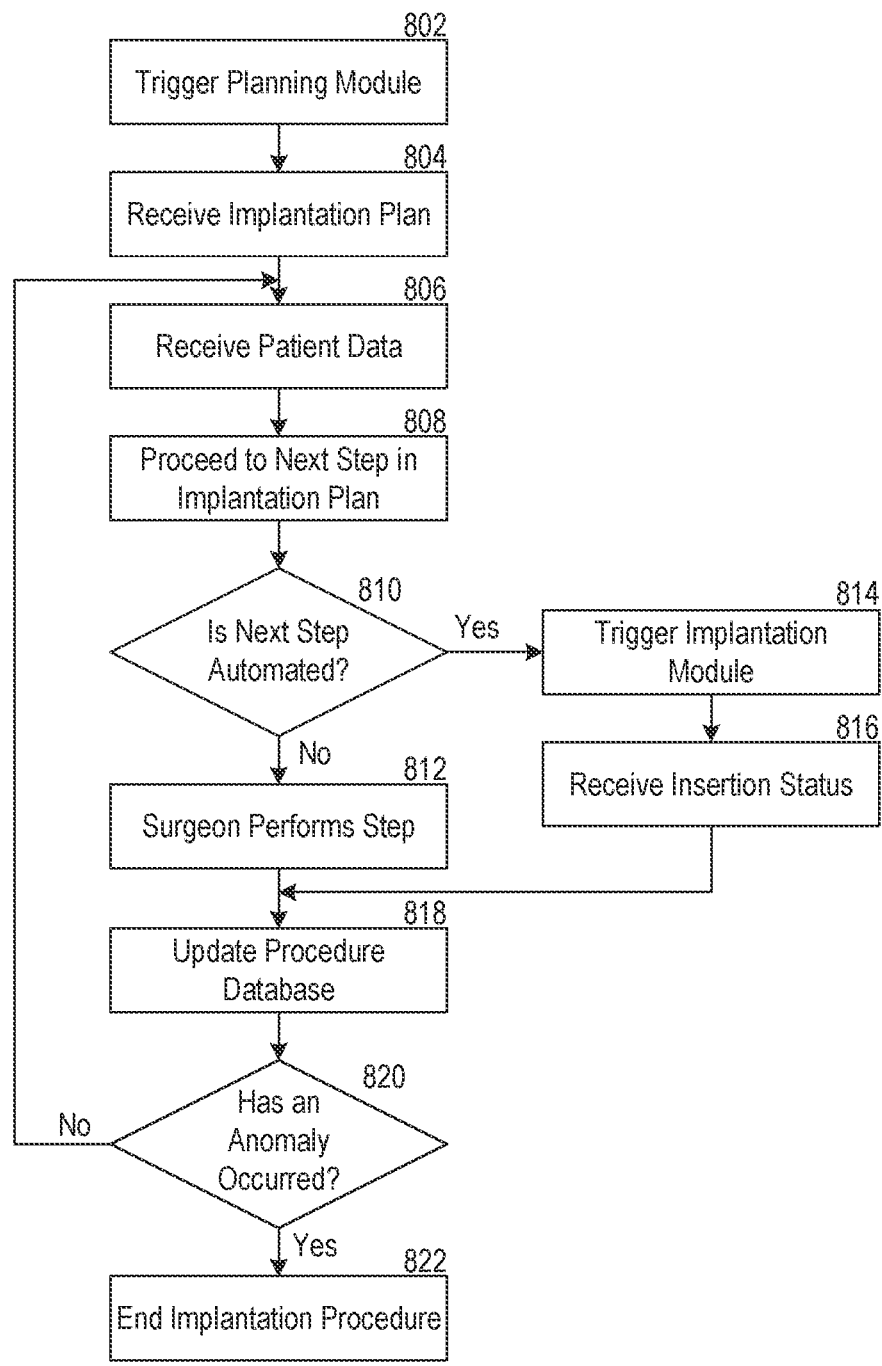
FIG. 8 is a flow diagram illustrating an example process for robotic insertion of surgical implants, in accordance with one or more embodiments.

FIG. 8 is a flow diagram illustrating an example process for robotic insertion of surgical implants, in accordance with one or more embodiments. In some embodiments, the process of FIG. 8 is performed by the implantation module 624. The implantation module 624 is illustrated and described in more detail with reference to FIG. 6. In other embodiments, the process of FIG. 8 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 802, the implantation module 624 triggers and passes control to the planning module 626 to create an implantation plan for the insertion of the surgical implant 616 using the surgical robot 602. The planning module 626, the surgical implant 616, and the surgical robot 602 are illustrated and described in more detail with reference to FIG. 6. The surgical robot 602 can be controlled autonomously or by an operator such as a surgeon. The planning module 626 generates a virtual model of a portion of the patient's body, selects the implant components 618, places the implant components 618 within the virtual model, and generates a surgical tool path to facilitate insertion of the surgical implant 616. The planning module 626 further generates insertion parameters for controlling the surgical robot 602 to implant an implant component 618 or perform another action during a surgical implant insertion procedure. The implant component 618 is illustrated and described in more detail with reference to FIG. 6.

In step 804, the implantation module 624 receives an implantation plan from the planning module 626. The implantation plan specifies at least one surgical implant 616 including at least one implant component 618, a placement of the implant components 618 in a virtual model of the patient's body, and the path for the surgical tools 154 and the implant components 618 within the body of the patient during the insertion procedure. The path can include steps or actions to be taken by a user device operated by a medical professional or autonomously by the surgical robot 602 or, alternatively, in a hybrid manner. The path can specify insertion parameters including a speed of the surgical tool head movement, a rotational speed of rotational tools, axial force exerted by a surgical tool 154, etc. In embodiments, inserting the at least one surgical implant component 618 includes altering, by the surgical robot 602, an alignment of the at least one surgical implant component 618 with respect to the implantation site. For example, an exemplary step of an implantation plan can specify inserting a screw into a bone of a patient to serve as an anchor point for the surgical implant 616. In this example, the step of inserting the screw is to be completed autonomously by the surgical robot 602. Continuing the example, the insertion parameters include a rotational speed of 10-30 rotations per minute, an axial force of 1-5 pounds per square inch, and an alignment angle of 15 degrees off perpendicular from the surface of the bone.

In step 806, the implantation module 624 receives patient data such as gender, age, height, weight, allergies, current and prior medical conditions, and any additional clinical information that can impact the outcome of the insertion procedure. The implantation module 624 can further acquire vital information such as the patient's blood pressure, heart rate, blood oxygen saturation, respiration rate, etc. The implantation module 624 can further acquire baseline vital information from clinical information or prior to initiating the insertion procedure. Vital information can be continuously or periodically acquired throughout the insertion procedure to monitor the patient's status. For example, the patient data can include an allergy to latex, chronic osteoporosis, and that the patient's heart rate is 65 beats per minute, blood pressure is 145/105, blood oxygen saturation is 99, and respirations are 6 breaths per minute.

In step 808, the implantation module 624 continues the implantation plan. The implantation plan includes steps or actions to be performed by a user device operated by a medical professional, autonomously by the surgical robot 602, or alternatively in a hybrid manner with actions performed by both the surgeon and the surgical robot 602. Such actions can involve a user device operated by a medical professional and the surgical robot 602 controlling separate robotic arms 604 in a synchronized manner. For example, the next step in an implantation plan can be the insertion of a screw to be completed autonomously by the surgical robot 602.

In step 810, the implantation module 624 determines whether the next step in the surgical procedure or implantation plan is to be performed autonomously by the surgical robot 602 or by a user device operated by a medical professional or another member of the surgical team such as a nurse. For example, the next step can be the insertion of a screw to be completed autonomously by the surgical robot 602. Alternately, the next step can be to make a 1-inch incision in the muscular tissue of the patient to be performed by a user device operated by a medical professional. Manual operations can further be completed via manual control of the surgical robot 602 by a user device operated by a medical professional, such that the surgical robot 602 performs the action to enhance stability by smoothing a surgeon's control inputs.

In some embodiments, one or more processors of the surgical system of FIG. 6 modify one or more of the insertion parameters based on a comparison of the insertion parameters to stored insertion parameters using a regression model. The stored insertion parameters are retrieved from the surgical procedure database 622. For example, in step 812, the implantation module 624 enables a user device operated by a medical professional to perform a step of the implantation plan when the step is determined to not be automated. For example, the surgeon makes a 1-inch incision in the patient's muscular tissue via manual control of the surgical robot 602. In step 814, the implantation module 624 triggers and passes control to the insertion module 628 when the next step is determined to be automated. The insertion module 628 is illustrated and described in more detail with reference to FIG. 6. The insertion module 628 uses patient data and data from the surgical procedure database 622 to modify or create insertion parameters, receive confirmation from a user device operated by a medical professional that the insertion parameters are acceptable, and proceed to insert the implant component 618 into the patient's body while monitoring the real-time insertion parameters to ensure measured insertion parameters are within an acceptable range of insertion parameter values approved by a user device operated by a medical professional. The surgical procedure database 622 is illustrated and described in more detail with reference to FIG. 6. In some embodiments, the insertion module 628 performs one or more of the steps discussed in connection with FIG. 9 during surgery. For example, to modify or create insertion parameters, the insertion module 628 can create a virtual model of the patient based on real-time imaging to position the implant or implant components within the subject. Prior to moving the implant, the insertion module 628 can place a virtual model of the implant in a virtual model of the patient's anatomy based on the real-time images. New or modified tool paths and insertion parameters can be generated based on the simulation. This process can be performed any number of times to complete a surgical step, or to perform and plan a next surgical step. If the measured insertion parameters exceed the approved insertion parameter values, the surgical robot 602 reevaluates the insertion parameters. For example, the insertion module 628 can be triggered to perform the automated insertion of a screw into the bone of a patient.

In step 816, the implantation module 624 receives an insertion status of an implant component 618 from the insertion module 628, confirming that the step being executed by the insertion module 628 has been completed. For example, the insertion status can include a confirmation that a screw has been successfully inserted into a bone of the patient. In step 818, the implantation module 624 updates the surgical procedure database 622 with a surgical step taken by either a user device operated by a medical professional, the surgical robot 602, or by coordinated actions of both the surgeon and the surgical robot 602. The surgical step is described by the action taken, any findings or anomalies that may have occurred and the insertion parameters, tool path used, etc. For example, the surgical procedure database 622 is updated with a step of the automated insertion of a screw into a bone of a patient by the surgical robot 602. The update includes the insertion parameters specifying a rotational speed of 10-30 rotations per minute, an axial force of 1-5 pounds per square inch, and an alignment angle of 15 degrees off perpendicular from the surface of the bone.

In step 820, the implantation module 624 determines whether the insertion is complete, an anomaly occurred, and/or an adverse event has been detected. The implant insertion is complete when no further steps remain to be performed by either a user device operated by a medical professional or the surgical robot 602 in the implantation plan. If the implant insertion is not complete, the implantation module 624 returns to step 806 and receives updated patient data that includes at least the patient's disposition and additional vital information, such as heart rate or blood pressure. In step 820, the implantation module 624 terminates the insertion procedure if the implant implantation is complete.

The methods discussed in connection with FIG. 8 can be used to perform surgical procedures that include both surgeon performance steps and automated steps. Patient data can be collected at the beginning of the surgical procedure and/or throughout surgery. For example, patient data can be recollected after completing a surgical step, a set of surgical steps, etc. In some embodiments, at step 806, patient data is received from, for example, patient monitoring equipment, visualization equipment, cameras, scanners, MRI machines, or the like. In step 808, a plan (e.g., a surgical plan, an implantation plan, etc.) can be evaluated to determine whether to perform the next step should be surgeon performed or robotically performed. Previous patient outcomes can be evaluated corresponding to that particular step. If the system determines that the next step should be automated, the implantation module is triggered at step 814. At step 816, the system can use the patient data to implement the next step. Historical data can be used to perform the next step based on insertion status. At step 818, a procedure database can be updated based on the performed step. This process can be repeated any number of times to sequentially perform steps of the plan. Referring again to step 810, if the system determines that the next step can be performed by a physician, the system can provide information to assist the physician. For example, the system can provide insertion parameters that can help guide the physician performed surgical step. After completing a step, the system can update the procedure database at step 818.

The method can include steps performed by other methods disclosed herein, such as the method discussed in connection with FIG. 9. For one or more of the steps discussed with respect to FIG. 8, the system can create virtual models of the procedures (virtual models of anatomy, implants, tools, etc.), modify implantation plans, generate surgical steps for implantation plans, generate tool paths and/or insertion parameters, or the like. For example, the implementation module can be triggered at step 814. One or more steps discussed in connection with FIG. 9 can be performed to generate updated tool paths and insertion parameters based on the patient data received at step 806. If the system determines that a suitable automated surgical step cannot be performed, the system can return to step 818 and notify the surgeon that the next step should be physician performed. At step 812, the surgeon can perform the next surgical step or a series of surgical steps.

Figure 9:
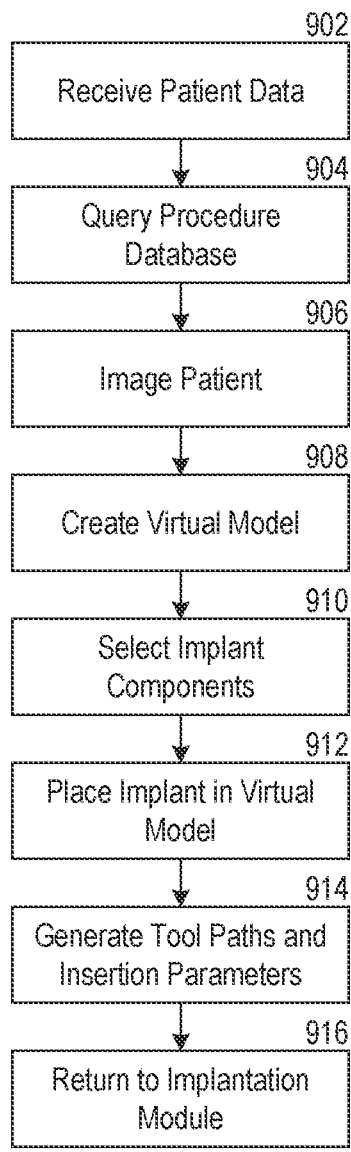
FIG. 9 is a flow diagram illustrating an example process for robotic insertion of surgical implants, in accordance with one or more embodiments.

FIG. 9 is a flow diagram illustrating an example process for a robotic surgical step or insertion of surgical implants, in accordance with one or more embodiments. In some embodiments, the process of FIG. 9 is performed by the planning module 626. The planning module 626 is illustrated and described in more detail with reference to FIG. 6. In other embodiments, the process of FIG. 9 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 902, the planning module 626 receives patient data from the implantation module 624. The implantation module 624 is illustrated and described in more detail with reference to FIG. 6. The patient data includes at least one of gender, age, height, weight, allergies, current and prior medical conditions, or additional clinical information that can impact the outcome of the insertion procedure. Patient data can additionally include vital information such as the patient's blood pressure, heart rate, blood oxygen saturation, respiration rate, etc. For example, the patient data can include the patient's vital information including a heart rate of 65 beats per minute, a blood pressure of 145/105, a blood oxygen saturation of 99, and respirations of 6 breaths per minute. Continuing the example, the planning module 626 further receives patient data specifying that the patient is female and has osteoporosis.

In step 904, the planning module 626 queries the surgical procedure database 622 for data from historical implant insertion procedures. The surgical procedure database 622 is illustrated and described in more detail with reference to FIG. 6. An insertion procedure specifies a series of steps or actions taken during surgical implant insertion. The steps or actions further include a surgical tool path, insertion parameters such as a direction and speed of movement of a surgical tool 154, and operational parameters such as a rotational speed, an axial force exerted by the surgical tool 154, or tool alignment. The surgical tools 154 are illustrated and described in more detail with reference to FIG. 1. A surgical step can further specify an implant component 618. The implant component 618 is illustrated and described in more detail with reference to FIG. 6. For example, a surgical step can specify the automated insertion of a screw into a bone of a patient by the surgical robot 602. The surgical robot 602 is illustrated and described in more detail with reference to FIG. 6. In this example, the surgical step further specifies the insertion parameters of rotational speed of 10-30 rotations per minute, an axial force of 1-5 pounds per square inch, and an alignment angle of 15 degrees off perpendicular from the surface of the bone.

In step 906, the planning module 626 enables imaging of at least a portion of the patient's body using at least one imaging device 614, e.g., using magnetic resonance imaging, computer aided tomography, or ultrasound. The at least one imaging device 614 is illustrated and described in more detail with reference to FIG. 6. The imaging includes at least the site receiving the surgical implant 616 and the surrounding area. Alternately, the imaging can include the entirety of the patient's body. For example, the patient is imaged using MRI (see FIG. 1), such that multiple images are taken representing slices at varying depths.

In step 908, the planning module 626 generates a virtual model of the patient's body using the images captured of at least a portion of the patient's body using the at least one imaging device 614. The virtual model can be two dimensional or three dimensional. Further embodiments can include a virtual model including a fourth dimension of time, such that the model can be animated with the movement of the patient's body over a period of time. For example, multiple magnetic resonance imaging slices can be layered to create a three-dimensional virtual model of the patient's spine and surrounding tissues in preparation of performing a spinal 360 fusion procedure via the insertion of an implant 616 fusing three vertebrae together. In other embodiments, imaging device 614 is a real time imaging device used during the procedure, such as an endoscope or other surgical imaging device. The imaging device 614 can update the virtual model of the patient's body during the procedure to create an updated virtual model of the patient's body. The updated model of the patient's body can thereby be used by the planning module 626 to select at least one of a plurality of surgical routes through the patient body to satisfy one or more criteria, the selection criteria may be, for example, safest route through the patient's body, fastest or most efficient route through the patient's body, least expensive route through the patient's body, or some other criteria.

In step 910, the planning module 626 selects the implant components 618, which will comprise the implant 616. The implant 616 can include a single implant component 618 or an assembly of multiple implant components 618. An assembly can be implanted as a single unit or can require insertion in multiple discrete pieces to form the final implant 616. Use of an assembly can improve functionality of the implant 616, such as allowing for articulation or flexibility, or can facilitate the insertion of the implant 616, such that the assembled implant 616 is rigid with little or no flexibility. Selection of the implant components 618 can further include selecting the materials from which each implant component 618 is to be made of. For example, the implant components 618 can include a spinal implant 616 that has six screws, each with a head known as a "tulip" to receive one of two rods, and two plates to join the two rods together to prevent movement relative to one another. In this example, all of the implant components 618 are made of titanium.

In step 912, the planning module 626 places at least one surgical implant 616 in or on the virtual model of the patient's body. The surgical implants 616 are placed in the virtual model as they would be in an ideal case by a surgeon or a surgical robot 602 in or on the patient's body. For example, a spinal implant is inserted into a three-dimensional model of a patient's thoracic spine to fuse three vertebrae to one another. In this example, the spinal implant 616 include at least two screws inserted 1 inch into each vertebra, one on either side of the spinous process and perpendicular to the surface of the vertebrae. Additionally, two rods located on either side of the spinous process are each secured to the screws on its respective side of the spinous process via a tulip. Two plates connect the two rods to one another to prevent the rods from moving relative to one another.

In step 914, the planning module 626 generates surgical tool path and insertion parameters to act as instructions for a user device operated by a medical professional or surgical robot 602 to aid the insertion of the implant components 618. The tool path can be manually defined or generated via a computer algorithm such that the tool path avoids nervous tissues, rigid bone structures, blood vessels, and any organs or tissues which should be avoided. Some features may need to be displaced during the surgical procedure, such as a portion of the bone removed, or an organ pushed aside to access the surgical site. A tool path is generated for each step, action, movement, etc., within the patient's body including surgical tools for creating incisions, managing bleeding, and maneuvering and inserting the implant components 618 into the patient's body. For example, a surgical tool path includes moving a rod for insertion along the spine of the patient into the incision site and parallel to the spine until it is in position alongside the spinous process and above the screws, and further engaging the rod with the tulip on the head of each screw. In this example, the planning module 626 further generates insertion parameters, such as the rate of movement of an implant component 618 within the patient's body, the orientation of the implant component 618, and the force applied to engage the rod with the screws. Continuing the example, the implant component 618 is moved within the patient's body by pushing a rod lengthwise into the incision to the surgical site until it is in position at a rate not to exceed 2 inches per minute and when positioned above the screws it is intended to engage, applying a force perpendicular to the rod not to exceed 10 pounds per square inch until the rod engages the screw heads.

In step 916, the planning module 626 returns control to the implantation module 624 when the implant components 618 have been selected, placed in a virtual model of the patient's body, and the surgical tool path and insertion parameters have been generated. The implant components 618, their placement, and the surgical tool path and insertion parameters make up an implant insertion plan.

A user (e.g., a surgical team, physician, etc.) can provide inputs to the process of FIG. 9. In some embodiments, a user reviews the tool paths and/or insertion parameters while viewing images of a simulation performed using the virtual model at step 912. During the surgical procedure, the system can monitor the insertion of the implant component to identify predetermined events. In response to identification of events, one or more of the insertion parameters can be modified for continuing the surgical step. The identified events can include, without limitation, identification of nominal insertion parameters, non-nominal insertion parameters, abnormal events, or the like. If nominal insertion parameters associated with completion are identified, the system can determine that the implant component is at the desired implanted position. The surgical system can then proceed to implant additional devices or complete other surgical steps.

The virtual model and simulations performed using virtual model can be displayed to a user for evaluation. The user can provide input and can modify surgical steps, the implantation plan, or the virtual model. In some embodiments, the user can reposition a model of the implant with respect to the virtual model of the anatomy. The system can then provide analytics associated with a repositioning. The analytics can include changes in predicted outcomes, proposed surgical steps of an updated implantation plan, tool paths, insertion parameters and other information useful for performing the surgery. The user can review the updated information to accept or reject the modification. This process can be repeated any number of times until a physician improved implantation plan and simulation is approved.

Figure 10:
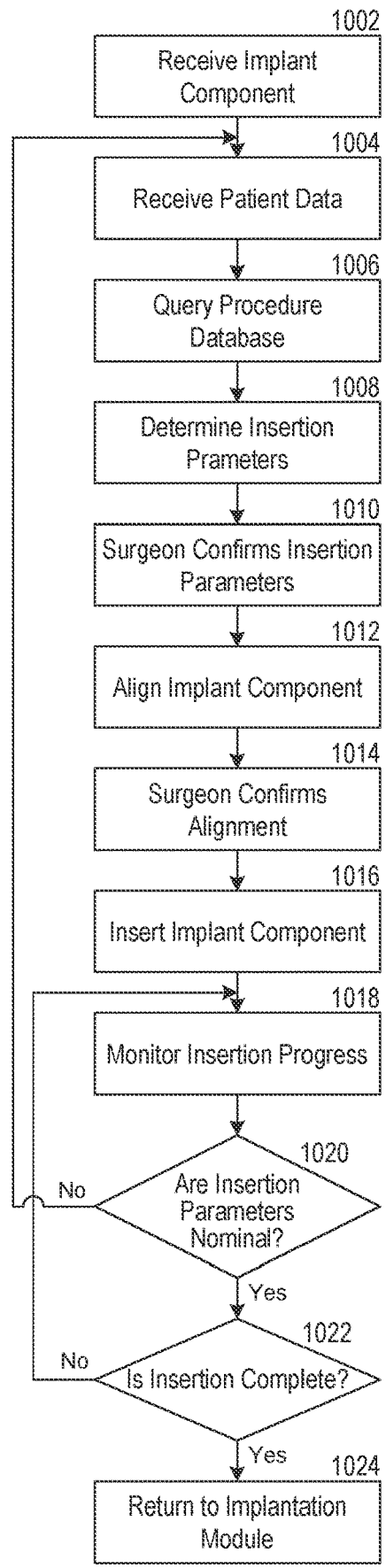
FIG. 10 is a flow diagram illustrating an example process for robotic insertion of surgical implants, in accordance with one or more embodiments.

FIG. 10 is a flow diagram illustrating an example process for robotic insertion of surgical implants, in accordance with one or more embodiments. In some embodiments, the process of FIG. 10 is performed by the insertion module 628. The insertion module 628 is illustrated and described in more detail with reference to FIG. 6. In other embodiments, the process of FIG. 10 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1002, the insertion module 628 receives information specifying one or more implant components 618 to be inserted into a patient's body. The one or more implant components 618 are illustrated and described in more detail with reference to FIG. 6. The insertion module 628 receives insertion parameters as indicated by a surgical implant insertion plan. In some embodiments, the insertion module 628 receives insertion parameters that specify movements for the surgical robot 602 or a surgeon that do not directly involve the implant component 618. For example, the insertion module 628 can receive information specifying a screw to be inserted into the T6 vertebra of the patient's body. In this example, the insertion module 628 can receive insertion parameters specifying a rotational speed of 10-30 rotations per minute, an axial force of 1-5 pounds per square inch, and an alignment angle of 15 degrees off perpendicular from the surface of the bone.

In step 1004, the insertion module 628 receives patient data, such as gender, age, medical conditions, or other clinical information that can impact the implant insertion procedure and vital information, such as the patient's blood pressure, heart rate, blood oxygen saturation, respiration rate, etc. The insertion module 628 can retrieve baseline vital information from stored clinical information or receive the baseline vital information prior to initiating the implant insertion procedure. In embodiments, vital information is continuously or periodically acquired throughout the insertion procedure to monitor the patient's status. For example, the patient data can specify chronic osteoporosis and that the patient's heart rate is 65 beats per minutes, blood pressure is 145/105, blood oxygen saturation is 99, and respirations are 6 breaths per minute.

In step 1006, the insertion module 628 queries the surgical procedure database 622 for data from previous insertion procedures. The data includes steps of previous implantation plans, previous patient data, and previous patient outcomes. The insertion module 628 searches for data pertaining to previous implant insertion procedures having similar characteristics to the current insertion procedure, e.g., previous implant insertion procedures having at least one of a similar surgical implant 616, implant components 618, implant location in the patient's body, or patient data, such as gender, age, or clinical data (e.g., medical conditions). The characteristics used to search for the data retrieved from the surgical procedure database 622 can be modified, such that a large enough data set is retrieved. In embodiments, the data retrieved is used to train an artificial intelligence (AI) to determine optimal insertion parameters or surgical steps for inserting the implant component 618 into the patient's body (see FIG. 2). For example, the insertion module 628 searches for all data for patients having osteoporosis.

In step 1008, the insertion module 628 determines the particular insertion parameters to be used for the insertion of the implant component 618 into the patient's body. The particular insertion parameters used can be the insertion parameters previously generated by the planning module 626. The planning module 626 is illustrated and described in more detail with reference to FIG. 6. Alternatively, the planning module 626 may not generate insertion parameters, and the particular insertion parameters can be previously generated by the insertion module 628 itself. The insertion module 628 can modify one or more of the insertion parameters using, e.g., a regression model. For example, the insertion module 628 can compare insertion parameters previously generated by the planning module 626 with insertion parameters stored in the procedure database 622.

In embodiments, modifying one or more of the insertion parameters includes determining an offset of the insertion parameters based on the comparison, applying the offset to the insertion parameters, and recursively altering the insertion parameters based on the stored insertion parameters using the regression model. For example, the insertion module 628 can determine an offset (e.g., offset value, offset percentage, offset ratio, etc.), use the offset to determine new insertion parameters, and recursively modify one or more or the insertion parameters in the surgical procedure database 622. For example, the insertion module 628 can determine offset values, determine new insertion parameters based on the offset values, and recursively modify one or more of the insertion parameters using the data in the surgical procedure database 622. In another example, a previously generated insertion parameter for a tool movement speed is 5-10 cm per minute and an insertion parameter for the tool movement speed used in a previous insertion procedure from the surgical procedure database 622 is 8 cm per minute. Continuing the example, the insertion module 628 determines an offset of 0.5 cm per second because the previously used tool speed of 8 cm per minute is 0.5 cm per minute faster than the midpoint of the range of 5-10 cm per minute, resulting in a new range of 5.5-10.5 cm per minute. Further, the insertion module 628 retrieves another movement speed of 7 cm per minute for a previous insertion procedure and applies a second offset of minus 0.5 cm per minute, resolving the range back to 10-15 cm per second. The insertion module 628 can also receive manufacturer data (e.g., instructions for use, insertion settings, forces, etc.) to determine parameters, values, etc. The example illustrates an embodiment of the method performed by the insertion module 628. More complex embodiments that use statistical models and algorithms can also be utilized to generate more accurate regression models. The regression models can incorporate patient outcomes and other data disclosed herein.

In step 1010, the insertion module 628 receives information from a user device operated by a medical professional confirming or approving the insertion parameters. The surgeon can confirm the insertion parameters by acknowledging a prompt from the surgical robot 602, or alternatively, the surgeon can passively review the insertion parameters and provide confirmation by not intervening in the insertion procedure. The surgical robot 602 is illustrated and described in more detail with reference to FIG. 6. For example, a user device operated by a medical professional receives a visual prompt from the surgical robot 602. The prompt specifies the insertion parameters for inserting a screw into the T6 vertebra of the patient's body. In this example, the insertion parameters include a rotational speed of 10-30 rotations per minute, an axial force of 1-5 pounds per square inch, and an alignment angle of 15 degrees off perpendicular from the surface of the bone. Continuing the example, the surgeon further selects a confirmation button located on the surgical robot 602, allowing the surgical robot 602 to proceed.

In step 1012, the insertion module 628 aligns the implant component 618 or surgical tool 154 with the insertion site according to the insertion parameters. The surgical tool 154 is illustrated and described in more detail with reference to FIG. 1. The alignment specifies at least one of a point towards which the implant component 618 or surgical tool 154 should be oriented, an angle measured from the perpendicular at which the implant component 618 or surgical tool 154 should be oriented towards the point using an axis perpendicular to a surface of the bone or other surface on or within the patient's body as reference, or the primary axis of the implant component 618 or surgical tool 154 terminating at the point closest to the patient as the orientation line. For example, a screw can be aligned to the T6 vertebra of the patient at an alignment angle of 15 degrees off the perpendicular axis with the surface of the bone.

In step 1014, the insertion module 628 receives confirmation of the alignment from a surgeon or a user device operated by a medical professional. The surgeon can confirm by acknowledging a prompt by the surgical robot 602, or alternatively, passively monitor the surgical robot 602's actions and may intervene at any point. A prompt provided to a user device operated by a medical professional can include any of a visual, audible, or haptic notification. For example, a surgeon passively monitoring the surgical robot 602's actions approves the alignment by not acting to prevent the surgical robot 602 from continuing the procedure. The surgical robot 602 can pause after aligning the implant component 618 or surgical tool 154 to provide an opportunity for the surgeon to review the alignment using a user device operated by the surgeon. Further, the surgeon can delay an action without rejecting it to provide additional time to review the alignment.

In step 1016, the insertion module 628 inserts or implants the implant component 618 into the patient's body as indicated by the insertion parameters. For example, the insertion module 628 inserts or implants a screw into the T6 vertebra of a patient's body by rotating the screw at a rate of 25 rotations per minute and applying an axial force of 3 pounds per square inch. In step 1018, the insertion module 628 monitors the insertion progress of the implantation or insertion of the implant component 618. In embodiments, the insertion module 628 monitors a current position of the implant component 618 or surgical tool 154, a rate of movement, or additional variables described by the insertion parameters. For example, a screw being inserted into the T6 vertebra has reached a depth of 0.5 inches. The target depth is 1 inch and the screw is rotating at a rate of 25 rotations per minute. An axial force of 4 pounds per square inch is being applied to the screw. A surgeon can additionally monitor the insertion progress by observing the surgical robot 602's actions and/or the current insertion parameters.

In step 1020, the insertion module 628 determines whether the current insertion parameters are nominal or non-nominal. Nominal refers to the current insertion parameters being within the ranges specified by the insertion parameters as determined in step 1008 and confirmed by a surgeon in step 1010. In embodiments, a surgeon monitors the current insertion parameters and determines whether the current insertion parameters are acceptable regardless of whether they are within the insertion parameter ranges previously determined and approved (conformed). For example, the current insertion parameters for the insertion of a screw into the T6 vertebra can include the screw reaching a depth of 0.75 inches, the screw rotating at a rate of 25 rotations per minute, and an axial force of 4 pounds per square inch being applied to the screw. In this example, the depth is less than 1 inch, which is within the nominal range. Additionally, the rotational rate of 25 rotations per minute is within the range of 10-30 rotations per minute, and the axial force of 4 pounds per square inch is within the acceptable range of 1-5 pounds per square inch. Therefore, the current insertion parameters are determined to be nominal by the insertion module 628. In another example, the axial force can be 6 pounds per square inch, which exceeds the acceptable maximum limit of 5 pounds per square inch. The surgical robot 602 ceases its current action in response to the current insertion parameters exceeding the nominal range. Alternately, a surgeon takes manual control of the surgical robot 602. The surgeon can proceed to complete the surgical step manually or allow the surgical robot 602 to reevaluate the situation and make another attempt by returning to step 1004 and re-evaluating the patient's current condition.

In step 1022, the insertion module 628 determines whether the insertion of the implant component 618 is complete. The insertion is determined to be complete when the target depth is reached. Alternately, the insertion is determined to be complete when the desired end position of a surgical tool 154 or another specified end result is reached. The surgical tool 154 is illustrated and described in more detail with reference to FIG. 1. In some embodiments, the completion of the insertion process is identified when the system determines that the implant component 618 is at a desired position. In some embodiments, the system can analyze one or more images of the implant component 618 within the patient. The images can be compared to prior patient images to evaluate the implant position. For example, prior patient images that substantially match the current patient images are identified. The outcomes of the identified prior patients are evaluated to confirm whether the implant component 618 is at the desired position. Alternately, the insertion can be determined to be complete when a surgeon determines that the insertion procedure is complete and enters a completion confirmation at the surgical robot 602. In step 1024, the insertion module 628 returns control to the implantation module 624 when the insertion procedure is determined to be complete. The implantation module 624 is illustrated and described in more detail with reference to FIG. 6. The insertion module 628 provides an insertion status to the implantation module 624, confirming that the insertion procedure has been completed.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

What is claimed is:

1. A method performed by a surgical system, comprising:
    receiving, by one or more computer processors of the surgical system, images of at least a portion of a patient's body for inserting a surgical implant in the patient's body, the surgical implant comprising at least one surgical implant component;
    generating, by the one or more computer processors, a virtual model of the at least a portion of the patient's body based on the images, the virtual model representing at least an implantation site for the surgical implant;

generating, by the one or more computer processors, an implantation plan based on the virtual model, the implantation plan comprising insertion parameters for controlling a surgical robot of the surgical system;

modifying, by the one or more computer processors, one or more of the insertion parameters based on a comparison of the insertion parameters to stored insertion parameters using a regression model, the stored insertion parameters retrieved from a surgical procedure database; and causing, by the one or more computer processors, the surgical robot to insert the at least one surgical implant component in the patient's body in accordance with the insertion parameters.

2. The method of claim 1, wherein modifying the one or more of the insertion parameters comprises:

determining, by the one or more computer processors, an offset value of the one or more of the insertion parameters based on the comparison;

applying, by the one or more computer processors, the offset value to the one or more of the insertion parameters; and recursively altering, by the one or more computer processors, the one or more of the insertion parameters based on the stored insertion parameters using the regression model.

3. The method of claim 1, wherein causing the surgical robot to insert the at least one surgical implant component comprises causing, by the one or more computer processors, the surgical robot to control at least one of:

a path of the at least one surgical implant component in the patient's body based on the insertion parameters;

an orientation of the at least one surgical implant component in the patient's body based on the insertion parameters; or an axial force applied to the at least one surgical implant component in the patient's body based on the insertion parameters.

4. The method of claim 1, wherein inserting the surgical implant comprises causing, by the one or more computer processors, the surgical robot to control at least one of a path or a speed of a surgical tool of the surgical system in the patient's body based on the insertion parameters.

5. The method of claim 1, wherein generating the implantation plan comprises:

placing, by the one or more computer processors, a model of the surgical implant in the virtual model of the at least a portion of the patient's body;

generating, by the one or more computer processors, one or more paths to virtually insert the model of the surgical implant at the implantation site in the virtual model; and identifying, by the one or more computer processors, the one or more of the insertion parameters based on a target position of the model of the surgical implant at the implantation site in the virtual model.

6. The method of claim 5, further comprising:

performing, by the one or more computer processors, a virtual robotic surgical procedure for the surgical robot according to the implantation plan to virtually insert the at least one surgical implant component at the implantation site using the one or more paths;

causing, by the one or more computer processors, a user interface of the surgical system to display at least a portion of the virtual robotic surgical procedure for user review;

receiving, by the one or more computer processors, input from the user; and modifying, by the one or more computer processors, the implantation plan based on the received input.

7. The method of claim 1, wherein inserting the at least one surgical implant component comprises:

receiving, by the one or more computer processors, user confirmation for the insertion parameters;

monitoring, by the one or more computer processors, insertion of the at least one surgical implant component to identify non-nominal insertion parameters and nominal insertion parameters, wherein modifying the one or more of the insertion parameters is performed in response to identifying the non-nominal insertion parameters, the modifying the one or more of the insertion parameters for continuing the insertion; and determining, by the one or more computer processors, that the at least one surgical implant component has been inserted at the target location based on the identified nominal insertion parameters.

8. A surgical system comprising:

one or more computer processors; and a non-transitory computer-readable storage medium storing computer instructions, which when executed by the one or more computer processors, cause the surgical system to:

receive images of at least a portion of a patient's body for inserting a surgical implant in the patient's body, the surgical implant comprising at least one surgical implant component;

generate a virtual model of the at least a portion of the patient's body based on the images, the virtual model representing at least an implantation site for the surgical implant;

generate an implantation plan based on the virtual model, the implantation plan comprising insertion parameters for controlling a surgical robot of the surgical system;

modify one or more of the insertion parameters based on a comparison of the insertion parameters to stored insertion parameters using a regression model, the stored insertion parameters retrieved from a surgical procedure database; and cause the surgical robot to insert the at least one surgical implant component in the patient's body in accordance with the insertion parameters.

9. The surgical system of claim 8, wherein the computer instructions to modify the one or more of the insertion parameters cause the surgical system to:

determine an offset value of the one or more of the insertion parameters based on the comparison;

apply the offset value to the one or more of the insertion parameters; and recursively alter the one or more of the insertion parameters based on the stored insertion parameters using the regression model.

10. The surgical system of claim 8, wherein the computer instructions to cause the surgical robot to insert the at least one surgical implant component cause the surgical robot to control at least one of:

a path of the at least one surgical implant component in the patient's body based on the insertion parameters;

an orientation of the at least one surgical implant component in the patient's body based on the insertion parameters; or an axial force applied to the at least one surgical implant component in the patient's body based on the insertion parameters.

11. The surgical system of claim 8, wherein the computer instructions to insert the surgical implant cause the surgical robot to control at least one of a path or a speed of a surgical tool of the surgical system in the patient's body based on the insertion parameters.

12. The surgical system of claim 8, wherein the computer instructions to generate the implantation plan cause the surgical system to:

place a model of the surgical implant in the virtual model of the at least a portion of the patient's body;

generate one or more paths to virtually insert the model of the surgical implant at the implantation site in the virtual model; and identify the one or more of the insertion parameters based on a target position of the model of the surgical implant at the implantation site in the virtual model.

13. The surgical system of claim 12, wherein the computer instructions further cause the surgical system to:

perform a virtual robotic surgical procedure for the surgical robot according to the implantation plan to virtually insert the at least one surgical implant component at the implantation site using the one or more paths;

cause a user interface of the surgical system to display at least a portion of the virtual robotic surgical procedure for user review;

receive input from the user; and modify the implantation plan based on the received input.

14. The surgical system of claim 8, wherein the computer instructions to insert the at least one surgical implant component cause the surgical system to:

receive user confirmation for the insertion parameters;

monitor insertion of the at least one surgical implant component to identify non-nominal insertion parameters and nominal insertion parameters, wherein modifying the one or more of the insertion parameters is performed in response to identifying the non-nominal insertion parameters, the modifying the one or more of the insertion parameters for continuing the insertion; and determine that the at least one surgical implant component has been inserted at the target location based on the identified nominal insertion parameters.

15. A non-transitory computer-readable storage medium storing computer instructions, which when executed by one or more computer processors, cause the one or more computer processors to:

receive images of at least a portion of a patient's body for inserting a surgical implant in the patient's body, the surgical implant comprising at least one surgical implant component;

generate a virtual model of the at least a portion of the patient's body based on the images, the virtual model representing at least an implantation site for the surgical implant;

generate an implantation plan based on the virtual model, the implantation plan comprising insertion parameters for controlling a surgical robot of the surgical system;

modify one or more of the insertion parameters based on a comparison of the insertion parameters to stored insertion parameters using a regression model, the stored insertion parameters retrieved from a surgical procedure database; and cause the surgical robot to insert the at least one surgical implant component in the patient's body in accordance with the insertion parameters.

16. The non-transitory computer-readable storage medium of claim 15, wherein the computer instructions to modify the one or more of the insertion parameters cause the one or more computer processors to:

determine an offset value of the one or more of the insertion parameters based on the comparison;

apply the offset value to the one or more of the insertion parameters; and recursively alter the one or more of the insertion parameters based on the stored insertion parameters using the regression model.

17. The non-transitory computer-readable storage medium of claim 15, wherein the computer instructions to cause the surgical robot to insert the at least one surgical implant component cause the surgical robot to control at least one of:

a path of the at least one surgical implant component in the patient's body based on the insertion parameters;

an orientation of the at least one surgical implant component in the patient's body based on the insertion parameters; or an axial force applied to the at least one surgical implant component in the patient's body based on the insertion parameters.

18. The non-transitory computer-readable storage medium of claim 15, wherein the computer instructions to insert the surgical implant cause the surgical robot to control at least one of at least one of a path or a speed of a surgical tool of the surgical system in the patient's body based on the insertion parameters.

19. The non-transitory computer-readable storage medium of claim 15, wherein the computer instructions to generate the implantation plan cause the one or more computer processors to:

place a model of the surgical implant in the virtual model of the at least a portion of the patient's body;

generate one or more paths to virtually insert the model of the surgical implant at the implantation site in the virtual model; and identify the one or more of the insertion parameters based on a target position of the model of the surgical implant at the implantation site in the virtual model.

20. The non-transitory computer-readable storage medium of claim 19, wherein the computer instructions cause the one or more computer processors to:

perform a virtual robotic surgical procedure for the surgical robot according to the implantation plan to virtually insert the at least one surgical implant component at the implantation site using the one or more paths;

cause a user interface of the surgical system to display at least a portion of the virtual robotic surgical procedure for user review;

receive input from the user; and modify the implantation plan based on the received input.

* * * * *